United States Patent [19]

Ostapchenko

[11] Patent Number: 5,081,161

[45] Date of Patent: Jan. 14, 1992

[54] PROCESS FOR MAKING SHAPED ARTICLES OF A THERMOPLASTIC RESIN HAVING A MICROCELLULAR STRUCTURE

[75] Inventor: George J. Ostapchenko, Wilmington, Del.

[73] Assignee: E. I. Du Pont de Nemours and Company, Wilmington, Del.

[21] Appl. No.: 538,859

[22] Filed: Jun. 15, 1990

[51] Int. Cl.$^5$ .......................... C08J 9/26; C08L 67/02; C08G 63/183; C08G 63/672
[52] U.S. Cl. ...................... 521/61; 521/138; 521/182; 525/439; 524/539; 528/301; 428/36.5
[58] Field of Search .......................... 521/61, 138, 182; 525/439; 528/301; 524/539; 428/36.5

[56] References Cited

U.S. PATENT DOCUMENTS

| | | | |
|---|---|---|---|
| 3,907,926 | 9/1975 | Brown et al. | 524/539 |
| 3,929,950 | 12/1975 | Nakamura et al. | 264/49 |
| 4,515,841 | 5/1985 | Dyke | 521/61 |
| 4,725,481 | 2/1988 | Ostapchenko | 528/301 |
| 4,834,746 | 5/1989 | Kira | 623/1 |
| 4,912,141 | 3/1990 | Kronman | 521/61 |

FOREIGN PATENT DOCUMENTS 1092303 12/1980 Canada.
0143638 6/1985 European Pat. Off..
0271216 6/1988 European Pat. Off..

Primary Examiner—John Kight, III
Assistant Examiner—John Cooney
Attorney, Agent, or Firm—Paul R. Steyermark

[57] ABSTRACT

A process for producing an article of a synthetic resin material or a thermoplastic resin blend having a microcellular structure comprises dispersing in a solid thermoplastic resin matrix having hydrophilic functional groups a finely divided water-soluble material, shaping the resin matrix containing the water-soluble material into the desired article, and immersing the shaped article in water at a suitable temperature to cause the resin matrix to swell to an extent of at least about 50% by volume while wet. The immersion causes water to diffuse into the resin matrix and solvate the water-soluble material, which becomes encased in water-filled cells that have solid walls, are substantially closed, and do not form an interconnecting porous network.

Articles made by this process include, among others, vascular grafts and organoids.

28 Claims, 2 Drawing Sheets

PROCESS FOR MAKING SHAPED ARTICLES OF A THERMOPLASTIC RESIN HAVING A MICROCELLULAR STRUCTURE

BACKGROUND OF THE INVENTION

This invention relates to a process for making shaped articles of a thermoplastic resin having a microcellular structure, which articles are useful in diverse applications, including, i.a., vascular prosthetic devices, dialysis membranes, organoids (cellular polymer systems which deliver proteins or hormones such as, for example, insulin to diseased individuals), controlled drug release devices and other devices requiring controlled diffusion of water-soluble compounds.

Articles made from a variety of resins having cellular structure are known. The resin cells may be either open and interconnected or closed. In either case, the resin density is less than the density of the same noncellular resin.

Methods for producing thermoplastic articles having densities lower than the densities of the thermoplastic materials used to fabricate the articles include, i.a.. the use of foaming agents that release gases that expand the thermoplastic materials at their normal processing temperatures; the use of thermoplastic materials containing liquids or solids, or both, that can be removed by extraction or dissolution; and the technique of stretching thermoplastic films containing liquids or solids, or both, to produce interfacial voids, followed by extraction or dissolution. The methods that depend on extraction or dissolution require the formation of an interconnecting network of pores that allows removal of the dissolved liquids or solids.

The density value of such articles having cellular structure generally depends on the volume fraction of the material removed by extraction or dissolution. For example, if the thermoplastic article contains 50% by volume of extractable material, and the density of the starting thermoplastic polymer is 1 g/cm$^3$, then the density of the extracted, cellular, thermoplastic article would be about 0.5 g/cm$^3$. Density values lower than those predicted from volume fractions are obtained if voids are produced at the interface between the extractable solid and the thermoplastic matrix during fabrication or by stretching after fabrication.

It is desirable in certain applications, such as, for example, vascular grafts and organoids to use light but strong materials, which in such cases must also be biocompatible, but should not be porous to the extent of leaking blood or other fluids flowing therethrough. Accordingly, it would be advantageous to be able to make such articles from resins having a closed-cell or nearly closed-cell structure rather than a porous, open-cell structure.

SUMMARY OF THE INVENTION

According to the present invention, there is now provided a process for producing an article of a synthetic resin material having a microcellular structure, said process comprising:

(a) dispersing in a solid resin matrix consisting essentially of one or more thermoplastic resins a finely divided water-soluble material, the amount of the water-soluble material being about 6–65 weight percent of the total composition, and the water diffusion rate into said thermoplastic resin matrix under the process conditions being significantly greater than the diffusion rate out of the resin matrix of the water-soluble material when hydrated, (b) forming said resin matrix containing dispersed water-soluble material into the desired shape, and (c) immersing the resulting shaped article in water for a sufficient time and at a suitable temperature to cause the resin matrix to swell to an extent of at least about 50% by volume, while wet, the water-soluble material becoming hydrated and encased in water-filled cells that have solid walls, are substantially closed, and do not form an interconnecting porous network extending to a significant degree through the entire thickness of the walls of the article.

There also are provided articles made by the foregoing process.

DETAILED DESCRIPTION OF THE INVENTION

Definition

Figure 1:
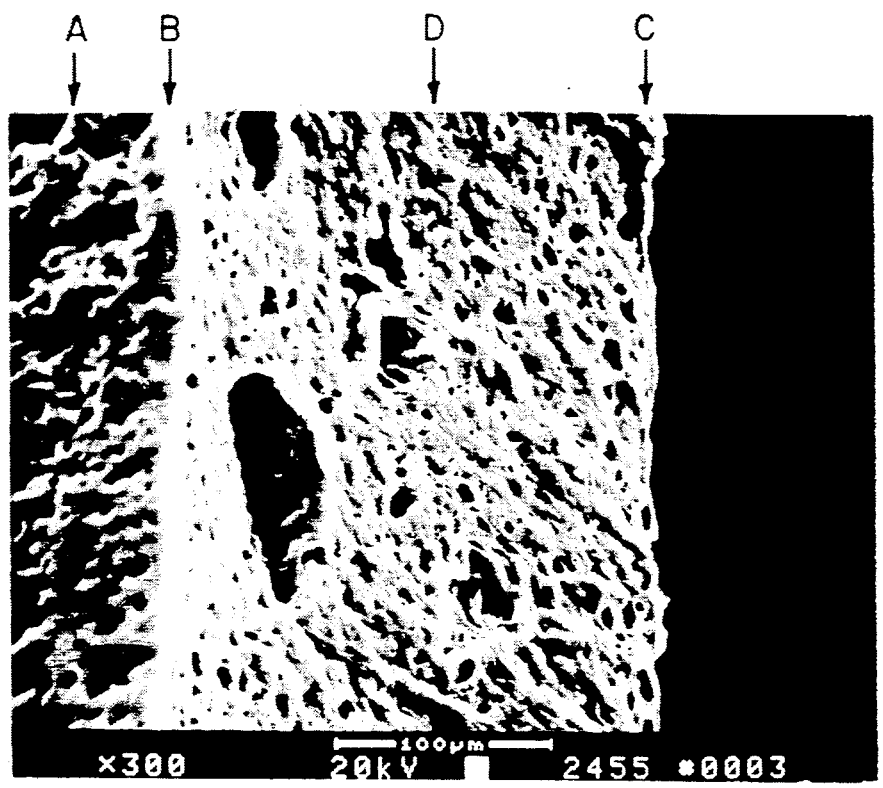
FIGS. 1 through 4 are photomicrographs of a cross-section of the wall of a microcellular tubing, being a shaped article of the present invention, taken through an electron microscope.

The term "consisting essentially", as employed in the present disclosure and claims, means that, in addition to the recited components, minor amounts of other components may also be present, so long as such other components do not detract from the operability of the invention.

The cellular resin structure of the articles of the present invention is produced by an osmotic pressure that is created when water is adsorbed into an article made of a suitable thermoplastic resin matrix containing a dispersed water-soluble material. Soft thermoplastic resins, as this term is normally understood in the polymer art, are more easily deformed by the osmotic pressure and produce cellular articles that have lower densities than hard thermoplastic resins. As the concentration of water-soluble material in the thermoplastic resin matrix increases, the tendency to form an interconnecting network also increases, causing a loss of solute. This reduces the osmotic pressure, resulting in a lower degree of resin matrix deformation and a higher density value. As the concentration of water-soluble material is decreased, the number of particles available for cell expansion is decreased, also resulting in a higher article density. The preferred amount of water-soluble material will be within the range of about 10–50% by weight. Naturally, the optimum amount of water-soluble material will depend on the material itself as well as on the thermoplastic resin. It is quite simple to establish by means of three experiments for a given thermoplastic resin matrix and a given water-soluble material the level of water-soluble material in the resin matrix for which maximum volume expansion and minimum density value are observed.

Suitable thermoplastic resins are those that have a low tensile modulus value at the process temperature. For example, thermoplastic resins that are to be used at room temperature preferably should have a tensile modulus of less than about 13.8 MPa at room temperature according to ASTM Standard D-638. Generally, suitable thermoplastic resins have some hydrophilic functional groups, such as, for example, amide, ester, ether, carboxyl, ionic carboxylate, and urethane. Preferably such resins will be elastomeric, as this term is understood in the art. All thermoplastic resins suitable for this application have sufficient water permeability at some temperature between room temperature and about 100° C. to permit water to diffuse through the resin material to the sites of the water-soluble material dispersed throughout the resin and to solvate the water-soluble material, so as to form closed cells containing a solution of particles of the water-soluble material in water. In addition to the requirement that the suitable resin have hydrophilic functional groups, the concentration of those functional groups must be sufficient to permit water diffusion to proceed to a satisfactory degree. This will, of course, depend to some extent on the chemical type of resin contemplated. For example, a copolyetherester which has a plurality of ethyleneoxy groups in its repeating units will be more permeable to water than a polyester which has no ethyleneoxy groups present in its repeating units. Conversely, thermoplastic resins that have a high degree of hydrophobicity will have low water permeablity.

One or more resins satisfying the conditions of low modulus and presence of hydrophilic groups may form the polymer matrix, so long as they can form homogeneous blends. In addition, small amounts of resins that may not satisfy such requirements also may be present in the resin matrix, so long as they form homogenous blends with the principal matrix resins, and so long as their presence does not interfere with water diffusion into the resin to the extent of inhibiting swelling of the resin matrix to the desired degree.

It has been found that the most suitable thermoplastic resin matrix for the purpose of this invention is a copolyetherester, which may be a copolyetherester elastomer commercially available from E. I. du Pont de Nemours and Company under the trademark HYTREL ®. This thermoplastic copolyetherester elastomer consists essentially of a multiplicity of recurring intralinear long chain and short chain ester units connected head-to-tail through ester linkages, said long chain ester units being represented by the formula

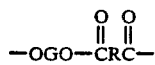 (I)

and short chain ester units being represented by the formula

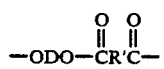 (II)

where G is a divalent radical remaining after the removal of terminal hydroxyl groups from a poly(alkylene oxide) glycol having an average molecular weight of 400 to 3500 and a ratio of the number of alkylene oxide carbon to oxygen atoms of 2 to 4.3, preferably 2.5 to 3.5; R and R' are divalent radicals remaining after removal of carboxyl groups from a dicarboxylic acid having a molecular weight less than 300; and D is a divalent radical remaining after the removal of hydroxyl groups from a diol having a molecular weight of less than about 250. Said copolyetherester has from about 25 to 80 weight percent of short-chain ester units (II).

A particularly suitable copolyetherester of this type is one which contains about 25 weight percent of repeating units (I) derived from 1,4-butylene terephthalate and 75 weight percent of repeating units (II) derived from poly(tetramethylene ether) glycol terephthalate. The poly(tetramethylene ether) glycol used to make the copolyetherester has a molecular weight of 2000. This particular resin will be designated herein as Copolyetherester A.

Another class of suitable thermoplastic materials are copolyamideetheresters, for example, those that can be made by a reaction of a polyamide with a poly(alkylene oxide) glycol.

The most practical water-soluble material to be hydrated according to the present invention is sodium chloride, especially that having a particle size of about 1–100 micrometers, particularly 10–20 micrometers. The preferred amount of sodium chloride in thermoplastic resin matrix is about 12–28 weight percent of the total composition. Of course, other particulate water-soluble materials can be used, including, for example, sodium carbonate, sodium sulfate, potassium chloride, potassium carbonate, magnesium chloride, etc., as well as various organic water-soluble materials, that are stable at the normal processing temperatures for the thermoplastic resin matrix, such as sucrose, glucose, urea, and various aminoacids or proteins. However, in biological applications such as, e.g., vascular grafts, such materials must be biocompatible since they can be expected to diffuse in time out of the resin to a larger or lesser degree and to enter into the stream of physiological fluids circulating in the organism of the patient.

In addition to the water-soluble material, the resin matrix may also contain other, water-insoluble fillers in an amount not exceeding about 10 weight percent, based on the total composition. Such fillers usually, but not necessarily, will be inorganic compounds, normally in a particulate, usually fine size, form and may include such materials as, e.g., calcium carbonate, calcium sulfate, barium sulfate, magnesium carbonate, titanium dioxide, zinc oxide, silica, carbon, pigments, etc. Of course, the presence of such additional fillers, which may or may not to some extent participate in the hydration step but are incapable of diffusing out of the resin, will decrease the amount of resin material available for expansion, so that both the increase of volume and the decrease of density may not be as great as in the absence of such filler material.

Blending of the thermoplastic resin or resins with the water-soluble material is carried out in solid state, that is, with the fully formed and isolated thermoplastic material, rather than with a precursor, a gel, a dispersion, or a solution of such material. Conventional blending equipment is used for this purpose, including V-blenders, ribbon blenders and drum tumblers. This is normally done at ambient temperature, but the resin preferably is first made into powder, for example, by cryogenic grinding. The mixture is fed to a mixing extruder (twin-screw or single screw, with an appropriate mixing head) and extruded into pellets to be later formed into the desired article; or, if more convenient, is extruded or molded directly into the desired article. Both the resin and the water-soluble material are first thoroughly dried and then, during those operations, protected from moisture, either by maintaining a nitrogen blanket over the blending equipment or over the feed hopper of the extruder, and preferably by carrying out the extrusion at a reduced pressure, so that any water vapor and other volatile materials can be evacuated.

The water-soluble compound can be hydrated within the resin matrix of the shaped article over a range of temperatures. At low temperatures, the rate of dissolution is slow, so that long times are required. In addition, the expansion of the cellular structure is usually not as great as the expansion at higher temperatures because the modulus of the thermoplastic resin is higher at lower temperatures. If the thermoplastic resin becomes very soft at or near the boiling point of water, the cellular structure may collapse giving a lower than expected expansion. If the thermoplastic resin crystallizes at the hydration temperature, cellular expansion will be hindered. It is to be noted that such hydration can in some cases be accomplished at a temperature above the melting point of the resin matrix, provided the resin matrix has a sufficient melt elasticity to maintain the integrity of the shaped article, as will be seen below. Accordingly, it can be seen that the choice of the operating temperature will be based to a large extent on the properties or behavior of the thermoplastic resin matrix within a given temperature range. One skilled in the art, familiar with the particular resin can readily predict the most suitable temperature. Otherwise, tests at different temperatures can be run to establish the most favorable temperature range.

This invention is now illustrated by representative examples of certain preferred embodiments thereof, where all parts, proportions, and percentages are by weight, unless otherwise indicated. All units of weight and measure other than SI units have been converted to SI units.

In all the examples, the water-soluble material was sodium chloride. The particular sodium chloride was obtained from Diamond Crystal Salt Co. (now part of AKZO Chemical, Inc.) as its Microsized ® G95-TCP Grade. This product, according to the manufacturer's data sheet, has the following particle size distribution, by screen analysis:

| Screen Opening, micrometers | Percent retained |
|---|---|
| 74 | 1 |
| 45 | 2 |
| 30 | 10 |
| 20 | 19 |
| 10 | 66 |
| Pan | 2 |

EXAMPLE 1

Pellets of Copolyetherester A having an average size of about 3 mm were cryogenically ground in a hammer mill to an average particle size of about 0.1 mm and dry mixed with sodium chloride, to give compositions having the percentages shown below in Table I. The mixture was fed into a Werner-Pfleiderer 28 mm twin-screw extruder and was extruded through a circular 4 mm die, to produce both rods about 1 m long and pellets about 3 mm thick. The rods were immersed in water either at room temperature for 3 days or at the boiling temperature for 3 hours. The percent volume increase of the rods was calculated from measurements taken before and after water immersion. The sodium chloride content was determined by ashing both before and after water immersion. The density of the rods was determined after water immersion by weighing in the wet and dry state. For the dry weight determination, the rods were dried for 2 hours at 80° C. in a vacuum oven. The results are tabulated below.

TABLE I

| Initial NaCl % | Water Immersion Conditions | | | | | |
|---|---|---|---|---|---|---|
| | 3 Days, Room Temp. | | | 3 Hours, Boiling | | |
| | % Vol. Incr. | Density g/cm$^3$ | Ash % | % Vol. Incr. | Density g/cm$^3$ | Ash % |
| 5.2 | 37 | 0.874 | 4.2 | 92 | 0.573 | 3.2 |
| 16.5 | 236 | 0.606 | 11.9 | 302 | 0.412 | 7.7 |
| 22.6 | 282 | 0.636 | 12.9 | 277 | 0.382 | 10.2 |
| 36.7 | 108 | 0.708 | 7.7 | 74 | 0.541 | 6.0 |

The above data show that when the sodium chloride content is varied from 5.2 to 36.7%, a maximum volume increase and a minimum density of the rods after water immersion are obtained at a sodium chloride content of about 16.5–22.6%. The ash content after water immersion shows that a higher percentage of sodium chloride is removed as its initial concentraton increases from 5.2 to 36.7%, suggesting the formation of an interconnecting network at high sodium chloride concentrations. The formation of an interconnecting network effectively reduces the time interval during which the osmotic pressure is operating to a sufficient degree to cause expansion of the rod-shaped articles.

EXAMPLE 2

Articles in the form of tubing were produced by extruding pellets described in Example 1, using a Haake 8.2 mm single screw extruder and a tubing die having an 11.4 mm outer diameter and a 6.4 mm inner diameter. The extruder and die were maintained at 200° C. The extrudate was drawn down to a tube of 4 mm outer diameter and was air cooled.

The following results were obtained after immersion in water.

TABLE II

| Initial NaCl Content, % | 3 Hours at boiling | | |
|---|---|---|---|
| | % Vol. Incr. | Density g/cm$^3$ | Ash % |
| 16.5 | 124 | 0.272 | 3.8 |
| 22.6 | 262 | 0.211 | 4.7 |
| 36.7 | 32 | 0.438 | 1.7 |

The data in Table II show the maximum volume increase and the minimum density at 22.6% of sodium chloride. The magnitude of the volume increase for tube-shaped articles is less than that obtained for rod-shaped articles because the larger surface area/volume ratio of the tubes allows a larger quantity of hydrated sodium chloride to diffuse out of the article per unit of time and thus reduces the time available for the osmotic pressure to expand the cellular structure.

EXAMPLE 3

Film-shaped articles were prepared by extruding pellets of thermoplastic Copolyetherester A containing 19.4% of sodium chloride in a 28 mm twin-screw extruder fitted with a slit die of a 254 cm width and a slot gap of 0.25 mm. Both the extruder and die were maintained at 200° C. The extrudate was cast onto a quench drum and wound on a paper core. After immersing the film in boiling water for 3 hours, the volume increase was 72%; the remaining ash content was 2.6%; and the film density was 0.296 g/cm$^3$. The surface area/volume ratio of the film is much greater than that of the rod-shaped articles, resulting in a smaller volume increase.

EXAMPLE 4

Other thermoplastic elastomers which were fabricated into microcellular rods had the indicated repeating units. Long chain units of copolyetheresters are designated by (I). Short chain units of copolyetheresters are designated by (II). For the purpose of this example, long chain units, whether of copolyetheresters or of copolyamideetheresters, are considered to be soft segments.

Copolyetherester B consisting of 35% of 1,4-butylene terephthalate (II) short chain units and 65% poly(tetramethylene ether) glycol (mol. wt. of 2000) terephthalate (I) long chain units. The ratio of carbon to oxygen atoms in the tetramethylene ether portion of the long chain units (I) was 4.0.

Copolyetherester C consisting of 20% of 1,4-butylene terephthalate (II), 8% of 1,4-butylene isophthalate (II), 52% of poly(tetramethylene ether) glycol (mol. wt. of 2000) terephthalate (I), and 20% of poly(tetramethylene ether) glycol (mol. wt. of 2000) isophthalate (I).

Copolyetherester D consisting of 60% of 1,4-butylene terephthalate (II) and 40% of poly(tetramethylene ether) glycol (mol. wt. of 1000) terephthalate (I).

Copolyamideetherester E consisting of 13% of poly(dodecamethylene adipamide) and 87% of soft segment poly(tetramethylene ether) glycol (mol. wt. of 2000) adipate.

Copolyetherester F consisting of 31% of 1,4-butylene terephthalate (II), 9% of 1,4-butylene isophthalate (II), 46.5% of ethylene oxide/propylene oxide copolyether terephthalate (I), and 13.5% of ethylene oxide/propylene oxide copolyether isophthalate (I). The ethylene oxide/propylene oxide glycol used to make the copolyetherester was obtained by end-capping poly(propylene ether) glycol with 30% of ethylene oxide and had a molecular weight of 2150. The ratio of carbon atoms to oxygen atoms in the ethylene oxide/propylene oxide portion of the long chain units (I) was 2.7.

Copolyamide G consisting of 8% of Nylon 66, 23% of poly(hexamethylene decyleneamide), 27% of poly(hexamethylene dodecylamide), and 42% of Nylon 6.

Sodium chloride was compounded with each one of the above thermoplastic resins, as described above, and the resulting compositions were fabricated into rods, as earlier described. The results of immersion experiments are tabulated below.

TABLE III

| Resin | Soft Segment, % | Init. NaCl, % | After 3 Hr. In Boiling Water | | |
|---|---|---|---|---|---|
| | | | % Vol. Increase | Density, g/cm³ | % Ash |
| G* | 0 | 24.9 | 27 | 1.00 | 11.7 |
| D | 40 | 20.7 | 69 | 0.668 | 12.8 |
| F | 60 | 23.6 | 648 | 0.444 | 6.5 |
| B | 65 | 19.4 | 192 | 0.449 | 10.4 |
| C | 72 | 26.5 | 362 | 0.334 | 9.6 |
| E | 87 | 28.6 | 695 | 0.217 | 9.6 |

*60° C. water immersion for 3 hours

The data in the above Table show that the resin expansion (% volume increase) after immersion in boiling water increases with the concentration of the soft segment in the starting thermoplastic resin. However, for a similar soft segment concentration, a greater expansion and a lower density were obtained for a resin having a lower ratio of carbon to oxygen atoms in the alkyleneoxy portion of the long chain units (I); see Copolyetherester F, as compared with Copolyetherester B. The water vapor transmission rates, according to ASTM D96-66, Procedure BW, were 2240 and 450 g/m² of surface area/24 hours for samples having a thickness of 25.4 micrometers of Copolyetheresters F and B, respectively.

EXAMPLE 5

Pellets comprising 54% of Copolyetherester A and 46% of sodium chloride were prepared as described in Example 1, fed to a 2.5 cm Wayne Machine Company single screw extruder, and extruded through a tubing die having an outer diameter of 0.25 mm and an inner diameter of 0.11 mm into a tubing, which was quenched in a water bath at room temperature. The tubing had an outer diameter of 4.2 mm and a wall thickness of 0.34 mm. After immersion in boiling water for three hours, the water-swollen tube had an outer diameter of 4.9 mm and a wall thickness of 0.5 mm. The volume expansion was 93%; the density was 0.483 g/cm3; and the ash content was 1.4%. No water leakage was detected through the tube walls after applying an internal pressure of 68.9 kPa for 30 minutes, indicating a non-porous cell structure. A water burst pressure of 276 kPa was measured, indicating high strength of the tubing.

The tubing was further washed with water at room temperature for 24 hours, sterilized by gamma irradiation, and seeded with canine endothelial cells. The seeded tubing was implanted as a canine carotid interposition graft. The graft was removed after 24 hours and found to be open and free of blood clots, indicating good biocompatibility and a low level of thromobogenicity.

Figure 2:
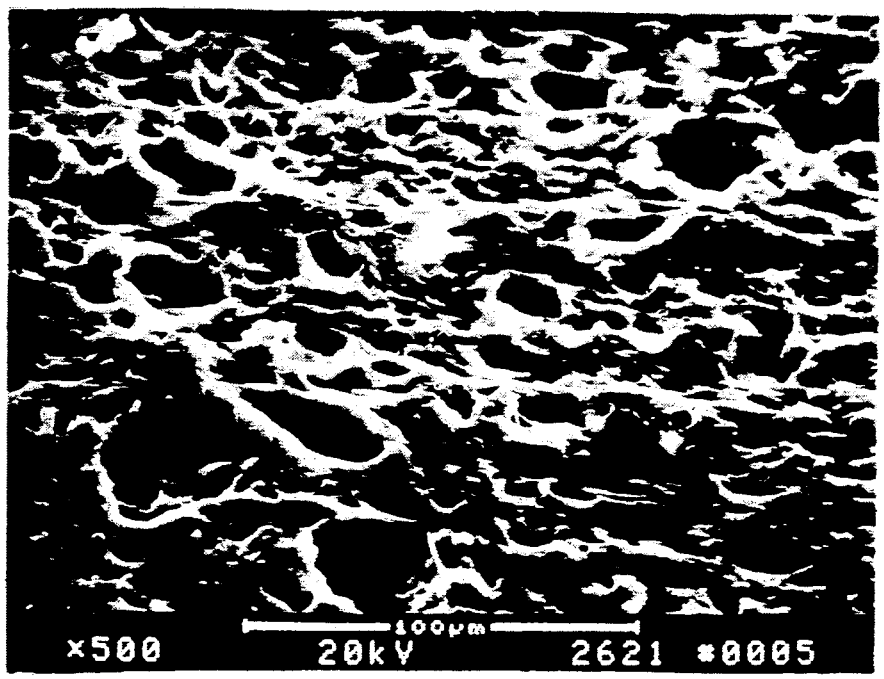
Figure 3:
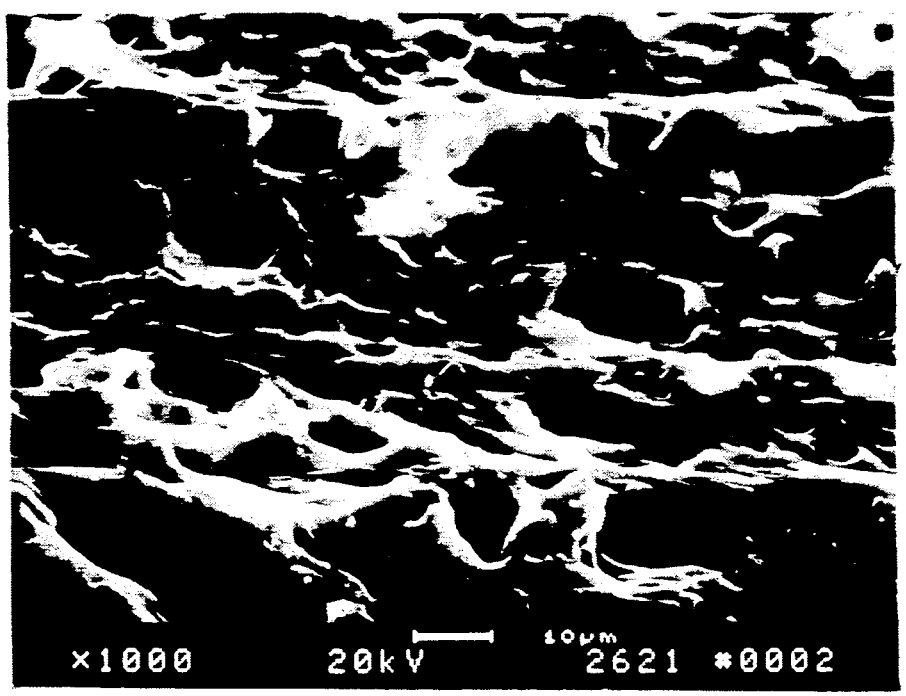
Figure 4:
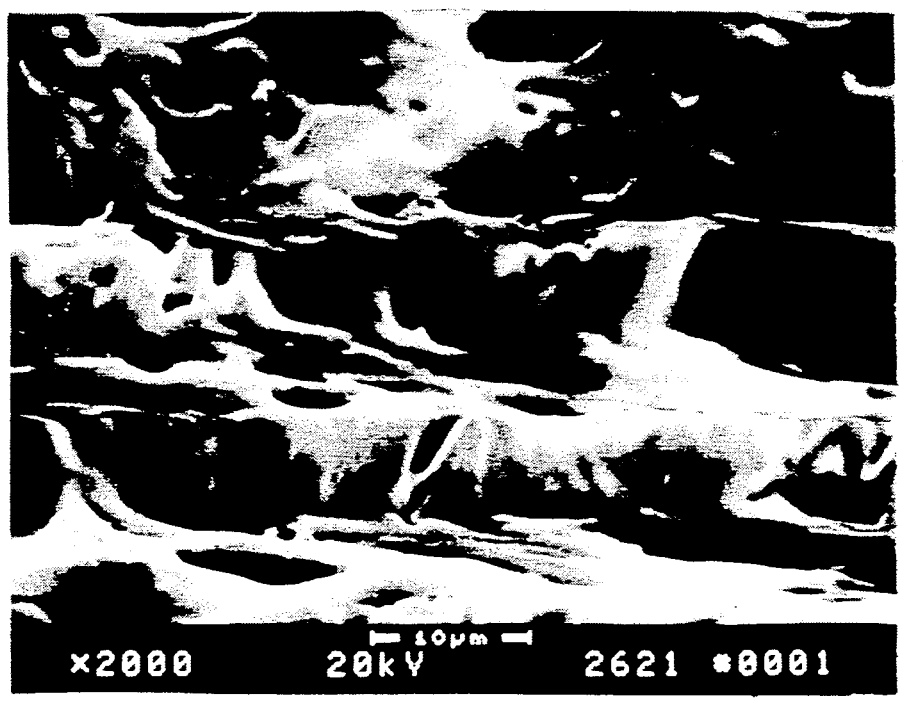

FIGS. 1 through 4 are photomicrographs of a longitudinal cross-section of the tubing made in this experiment through its lumen. The tubing had been dried before the section was made, so that some cells had collapsed. The specimens were immersed in liquid nitrogen and sectioned while still frozen. The magnifications are, respectively 300, 500, 1000, and 2000 times. In these photomicrographs, the dark portions are the microcells, while the light portions are the matrix resin material. In the 300x magnification photograph, FIG. 1, the inside surface, inside edge, and outside edge are designated, respectively, A, B, and C. The actual wall cross-section is designated D. The outside surface is below the plane of the picture and is not visible. FIGS. 2-4 show only a wall cross-section, corresponding to D of FIG. 1.

FIG. 1 does not show a continuous path from the inside to the outside of the tubing wall. FIGS. 2 through 4 show that the cell walls are solid (nonporous).

EXAMPLE 6

Rod-shaped articles were produced from a blend of a thermoplastic resin which was an ionomer with sodium chloride. The ionomer was a terpolymer of 67.5% of ethylene, 23.5% of n-butyl acrylate, and 9% of methacrylic acid, neutralized with zinc ions to an extent of 85%, and melting at about 75° C. The initial salt content was 21.7%. The rods were immersed for 3 hours in water, either at 80° C. or at boiling. The results are given below:

TABLE IV

| | At 80° C. | At boiling |
|---|---|---|
| Ash after immersion, % | 19.4 | 19.7 |

TABLE IV-continued

|  | At 80° C. | At boiling |
|---|---|---|
| Density, g/cm³ | 0.975 | 0.809 |
| Volume increase, % | 21 | 89 |

The above results show a salt loss of only about 2%, indicating a low diffusion rate of the hydrated salt through the ionomer. It can also be seen that volume increase at a temperature about 25° C. above the melting point of the ionomer was about four times larger than at a temperature about 5° C. above the ionomer melting point, reflecting the decrease in ionomer melt viscosity with increasing melt temperature. This ionomer resin has a sufficient melt elasticity to permit the article to maintain its integrity at temperatures moderately above the resin's melting point.

EXAMPLE 7

A blend of 2.5 parts of Copolyetherester A and 1 part of Copolyamideetherester E was further mixed with sodium chloride and extrude into pellets containing 28.1% of sodium chloride. The pellets were extruded into a tubing as described in Example 2. The tubing was immersed in boiling water for 3 hours. The volume expansion was 121%, and the ash content after immersion was 1.5%. The density of the dried tubing after immersion was 0.382 g/cm³.

This example shows that a blend of thermoplastic resins can be made into shaped articles having a microcellular structure. This provides a practical means of designing microcellular structures having specifically tailored properties.

I claim:

1. A process for producing an article of a synthetic resin material having a microcellular structure, said process comprising:
   (a) dispersing in a solid resin matrix consisting essentially of one or more thermoplastic resins a finely divided water-soluble material, the amount of the water-soluble material being about 6–65 weight percent of the total composition, and the water diffusion rate into said thermoplastic resin matrix under the process conditions being significantly greater than the diffusion rate out of the resin matrix of the water-soluble material when hydrated,
   (b) forming said resin matrix containing dispersed water-soluble material into the desired shape, and
   (c) immersing the resulting shaped article in water for a sufficient time and at a suitable temperature to cause the resin matrix to swell to an extent of at least about 50% by volume, while wet, the water-soluble material becoming hydrated and encased in water-filled cells that have solid walls, are substantially closed, and do not form an interconnecting porous network extending to a significant degree through the entire thickness of the walls of the article.

2. Process of claim 1 wherein the initial amount of water-soluble material is about 10–50 weight percent of the total composition.

3. Process of claim 1 wherein the water-soluble material is sodium chloride.

4. Process of claim 2 wherein the water-soluble material is sodium chloride.

5. Process of claim 4 wherein the initial amount of sodium chloride in the resin is about 12–28% of the total weight.

6. Process of claim 1 wherein the thermoplastic resin matrix consists essentially of one or more resins having one or more pendant or terminal hydrophilic groups selected from the group consisting of amide, ester, ether, carboxyl, ionic carboxylate, and urethane.

7. Process of claim 6 wherein the tensile modulus of the thermoplastic resin matrix, according to ASTM Standard D-638, is less than about 13.8 MPa at room temperature.

8. Process of claim 6 wherein the thermoplastic resin matrix consists essentially of a copolyetherester.

9. Process of claim 8 wherein the copolyetherester consists essentially of a multiplicity of recurring intralinear long chain and short chain ester units connected head-to-tail through ester linkages, said long chain ester units being represented by the formula

and short chain ester units being represented by the formula

where G is a divalent radical remaining after the removal of terminal hydroxyl groups from a poly(alkylene oxide) glycol having an average molecular weight of 400 to 3500 and a ratio of the number of alkylene oxide carbon to oxygen atoms of 2 to 4.3; R and R' are divalent radicals remaining after removal of carboxyl groups from a dicarboxylic acid having a molecular weight less than 300; and D is a divalent radical remaining after the removal of hydroxyl groups from a diol having a molecular weight of less than about 250, about 25 to 80 weight percent of all such units being short-chain ester units (II).

10. Process of claim 9 wherein the copolyetherester has a ratio of alkylene oxide carbon to oxygen atoms in the long units (I) of 2.5 to 3.5.

11. Process of claim 9 wherein the copolyetherester contains about 25 weight percent of repeating units (I) derived from 1,4-butylene terephthalate and 75 weight percent of repeating units (II) derived from poly(tetramethylene ether) glycol terephthalate, where the poly(tetramethylene ether) glycol portion has a molecular weight of about 2000.

12. Process of claim 6 wherein the thermoplastic resin matrix consists essentially of a copolyamideetherester.

13. A process of claim 1 wherein the immersion in water is carried out at the boiling temperature of water at normal pressure.

14. A shaped article made by the process of claim 1.
15. A shaped article made by the process of claim 2.
16. A shaped article made by the process of claim 3.
17. A shaped article made by the process of claim 4.
18. A shaped article made by the process of claim 5.
19. A shaped article made by the process of claim 6.
20. A shaped article made by the process of claim 7.
21. A shaped article made by the process of claim 8.
22. A shaped article made by the process of claim 9.
23. A shaped article made by the process of claim 10.
24. A shaped article made by the process of claim 11.
25. A shaped article made by the process of claim 6 which is a vascular graft.
26. A shaped article made by the process of claim 8 which is a vascular graft.
27. A shaped article made by the process of claim 9 which is a vascular graft.
28. A shaped article made by the process of claim 10 which is a vascular graft.

* * * * *